US009283131B2

(12) United States Patent
Belson et al.

(10) Patent No.: US 9,283,131 B2
(45) Date of Patent: Mar. 15, 2016

(54) PORTABLE TOPICAL OXYGEN THERAPY SYSTEM

(75) Inventors: Amir Belson, Los Altos, CA (US); James J. Leary, Fenton, MO (US)

(73) Assignee: Oxyvive, Inc., Los Altos, CA (US)

( * ) Notice: Subject to any disclaimer, the term of this patent is extended or adjusted under 35 U.S.C. 154(b) by 956 days.

(21) Appl. No.: 13/441,574

(22) Filed: Apr. 6, 2012

(65) Prior Publication Data
US 2012/0283626 A1   Nov. 8, 2012

Related U.S. Application Data

(63) Continuation of application No. PCT/US2010/002832, filed on Oct. 25, 2010.

(60) Provisional application No. 61/279,624, filed on Oct. 23, 2009, provisional application No. 61/516,952, filed on Apr. 11, 2011.

(51) Int. Cl.
*A61G 10/04* (2006.01)
*A61M 35/00* (2006.01)
(Continued)

(52) U.S. Cl.
CPC .............. *A61G 10/04* (2013.01); *A61M 35/00* (2013.01); *A61G 2007/05784* (2013.01); *A61H 23/02* (2013.01); *A61H 23/0236* (2013.01); *A61H 23/0245* (2013.01); *A61H 33/14* (2013.01); *A61H 2033/143* (2013.01);
(Continued)

(58) Field of Classification Search
CPC ............... A61G 10/04; A61G 2007/05784; A61M 35/00; A61H 33/14; A61H 23/0245; A61H 2033/143; A61H 2201/5058; A61H 2201/0207; A61H 23/02; A61H 2201/0214; A61H 23/0236
USPC .................................. 604/304–308; 606/192
See application file for complete search history.

(56) References Cited

U.S. PATENT DOCUMENTS 4,801,291 A    1/1989  Loori
5,154,697 A *  10/1992  Loori ............................ 604/23
(Continued)

FOREIGN PATENT DOCUMENTS

CN    201299708 Y    9/2009
GB      2409412 A    6/2005
(Continued)

OTHER PUBLICATIONS

WO 2006/114637, Blott et al.. date: 2006.*
(Continued)

*Primary Examiner* — Manuel Mendez
(74) *Attorney, Agent, or Firm* — Wilson Sonsini Goodrich & Rosati

(57) ABSTRACT

The present invention provides a topical oxygen therapy system for treating chronic non-healing wounds. The system is configured to be extremely portable, allowing patients to be completely ambulatory during treatment. The topical oxygen therapy system includes an oxygen source and a wound dressing capsule. The oxygen source includes a miniature compressed oxygen cylinder and a miniature pressure regulator that delivers oxygen through an outlet tube to the interior of the wound dressing capsule. The oxygen source may be attached directly to or integrated into the wound dressing capsule. Alternatively, the oxygen source and wound dressing capsule may be separate modules connected by a flexible tube.

25 Claims, 4 Drawing Sheets

(51) Int. Cl.
*A61H 23/02* (2006.01)
*A61H 33/14* (2006.01)
*A61G 7/057* (2006.01)

(52) U.S. Cl.
CPC ............... *A61H 2201/0207* (2013.01); *A61H 2201/0214* (2013.01); *A61H 2201/5058* (2013.01)

(56) References Cited

U.S. PATENT DOCUMENTS

| | | | |
|---|---|---|---|
| 5,480,410 A * | 1/1996 | Cuschieri et al. | 606/213 |
| 5,578,022 A * | 11/1996 | Scherson et al. | 604/304 |
| 5,788,682 A | 8/1998 | Maget | |
| 6,513,523 B1 * | 2/2003 | Izuchukwu et al. | 128/202.19 |
| 6,840,951 B2 * | 1/2005 | de la Torre et al. | 606/213 |
| 6,872,196 B1 * | 3/2005 | Bryan | 604/305 |
| 7,981,098 B2 * | 7/2011 | Boehringer et al. | 604/313 |
| 8,048,046 B2 * | 11/2011 | Hudspeth et al. | 604/313 |
| 2002/0082566 A1 | 6/2002 | Stenzler | |
| 2006/0116620 A1 | 6/2006 | Oyaski | |
| 2007/0118096 A1 | 5/2007 | Smith et al. | |
| 2008/0003299 A1 | 1/2008 | Trotter et al. | |
| 2009/0076475 A1 | 3/2009 | Ross et al. | |
| 2009/0259171 A1 | 10/2009 | Joshi et al. | |
| 2009/0264807 A1 | 10/2009 | Haggstrom et al. | |
| 2009/0306609 A1 * | 12/2009 | Blott et al. | 604/305 |

FOREIGN PATENT DOCUMENTS

| | | |
|---|---|---|
| JP | 2005-058745 A | 3/2005 |
| JP | 3116002 U | 11/2005 |
| JP | 2009-189785 A | 8/2009 |
| WO | WO 94/21323 A1 | 9/1994 |
| WO | WO 2004/002393 A1 | 1/2004 |
| WO | WO 2009/126833 A2 | 10/2009 |

OTHER PUBLICATIONS

European search report dated May 6, 2013 for EP Application No. 10825337.8.
International search report and written opinion dated Apr. 18, 2011 for PCT/US2010/002832.

* cited by examiner

Side View

Top View

PORTABLE TOPICAL OXYGEN THERAPY SYSTEM

CROSS REFERENCE TO RELATED APPLICATIONS

This application is a continuation of International Application No. PCT/US2010/002832, filed Oct. 25, 2010, which claims the benefit of Provisional Application No. 61/279,624, filed Oct. 23, 2009, and Provisional Application No. 61/516, 952, filed Apr. 11, 2011, the contents of which are incorporated herein by reference in their entirety.

BACKGROUND OF THE INVENTION

Field of the Invention

The present invention relates to a topical oxygen therapy system and a method for treating chronic non-healing wounds. The system is configured to be extremely portable, allowing patients to be completely ambulatory during treatment.

The U.S. Centers for Disease Control and Prevention estimate that chronic non-healing wounds affect about 5.7 million patients per year in the U.S. at a total treatment cost of approximately $20 billion annually. Chronic non-healing wounds are often the result of diabetic ulcers, venous stasis ulcers, decubitus ulcers (bed sores, pressure sores), post-surgical infections and gangrenous lesions. Chronic wounds such as these can go for many months without healing. Amputation of a limb is a last resort treatment for chronic wounds that have become life threatening, for example because of infection or gangrene. Various therapies have been devised for accelerating the healing of chronic non-healing wounds:

Hyperbaric oxygen therapy—Patients are treated in a pressurized hyperbaric chamber, typically at 2 to 3 times atmospheric pressure, and allowed to breath 100% oxygen. While this therapy has been shown to be effective at accelerating healing of wounds, the therapy is expensive, largely because of the cost of building and operating the hyperbaric chamber. This therapy is also time consuming and inconvenient for the patient. The patient must travel to the hospital or clinic several times a week for treatment, each treatment session typically lasts a couple of hours, and it may require months of treatment before the wound is adequately healed.

Topical oxygen chamber—The affected area of the body is enclosed within a flexible or rigid chamber and the chamber is filled with 100% oxygen. The oxygen can be supplied by a compressed oxygen tank or an oxygen concentrator. This therapy is less costly than hyperbaric oxygen therapy and it is portable enough that some patients can undergo treatment at home.

However, it is still time consuming, requiring four 90 minute session per week, during which, the patient must remain immobile. Because this therapy is intermittent, it may not be as effective as it could be if applied more continuously.

Transdermal continuous oxygen therapy—A battery powered electrochemical oxygen concentrator supplies 100% oxygen through a small flexible cannula that is inserted under a bandage placed over the wound. The electrochemical oxygen concentrator is described in U.S. Pat. No. 5,578,022 for Oxygen Producing Bandage and Method. The therapy is continuous for up to 15 days and the oxygen concentrator is very small allowing the patient to be completely ambulatory. However, the flow rate of oxygen from the oxygen concentrator is very low, only 3 ml per hour, and the entire disposable oxygen concentrator must be replaced every 7 to 15 days, adding significantly to the cost of the therapy. The current cost of a 15 day disposable oxygen concentrator is $700 or approximately $47 per day of treatment.

Accordingly, it would be beneficial to provide a topical oxygen therapy system for treating chronic non-healing wounds that is extremely portable, that allows patients to be completely ambulatory during treatment, that provides for a variety of treatment regimens and that has the potential to provide more economical treatment of chronic non-healing wounds.

DESCRIPTION OF THE INVENTION

The present invention provides a topical oxygen therapy system for treating chronic non-healing wounds. The system is configured to be extremely portable, allowing patients to be completely ambulatory during treatment.

Figure 1:
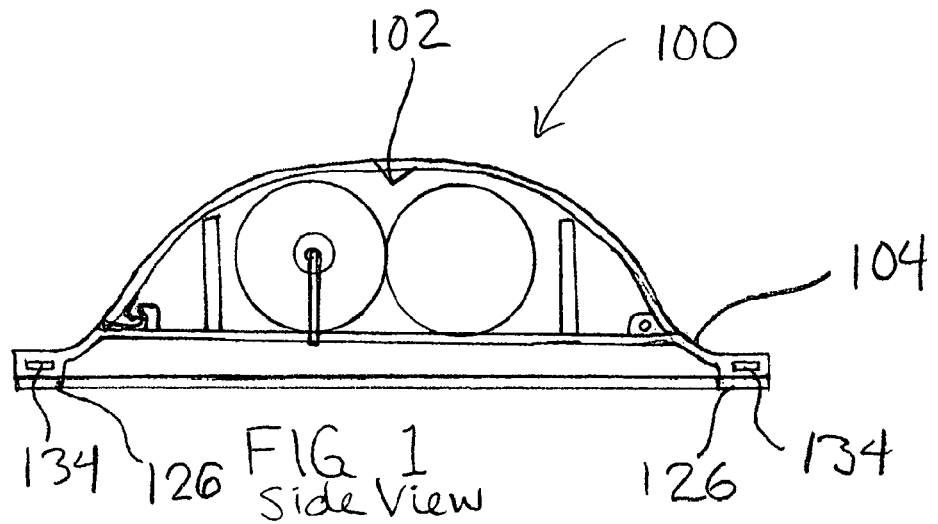
FIG. 1 is a cutaway side view of a topical oxygen therapy system according to the present invention.
Figure 2:
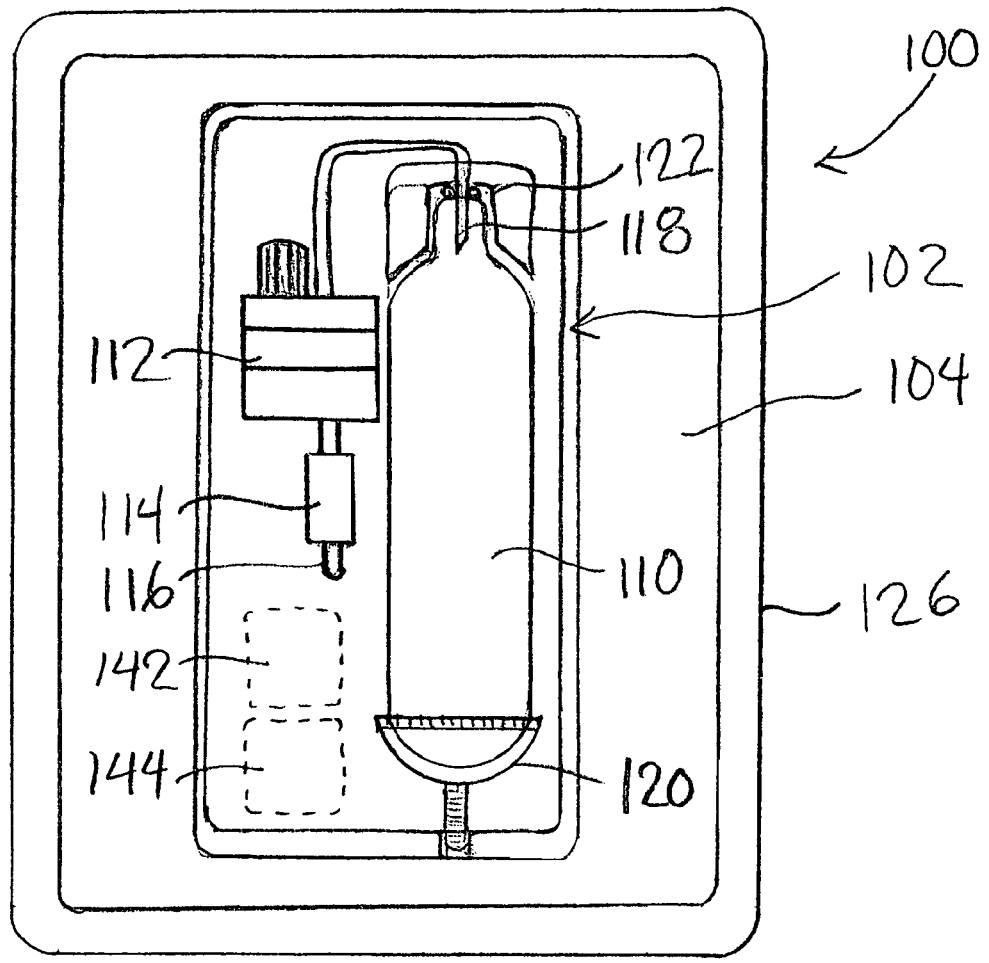
FIG. 2 is a top view of the topical oxygen therapy system of FIG. 1 with a contoured protective housing removed to show the oxygen source inside.
Figure 3:
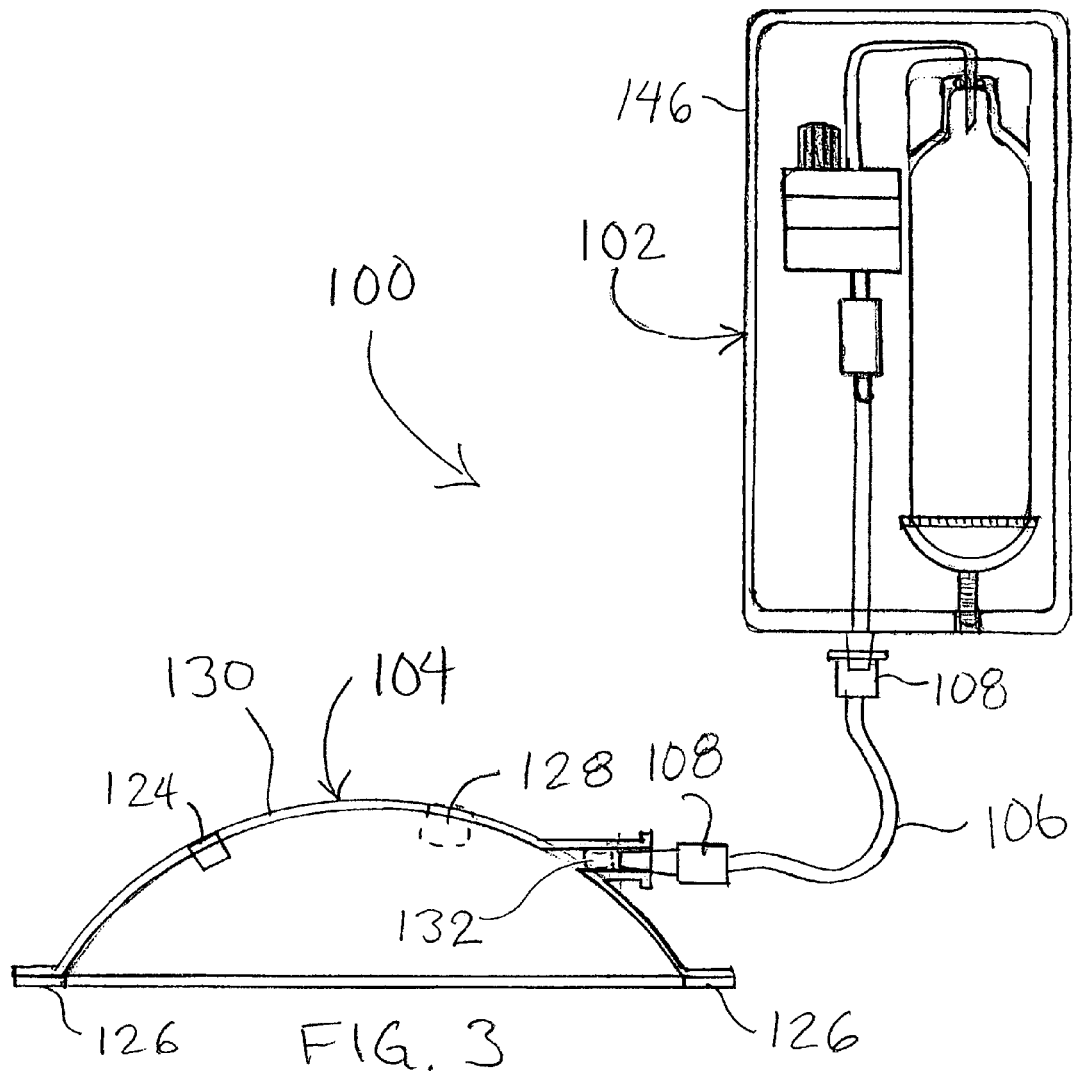
FIG. 3 shows a wound dressing capsule in the shape of a rigid or semi-rigid dome connected to the oxygen source by a flexible.
Figure 4:
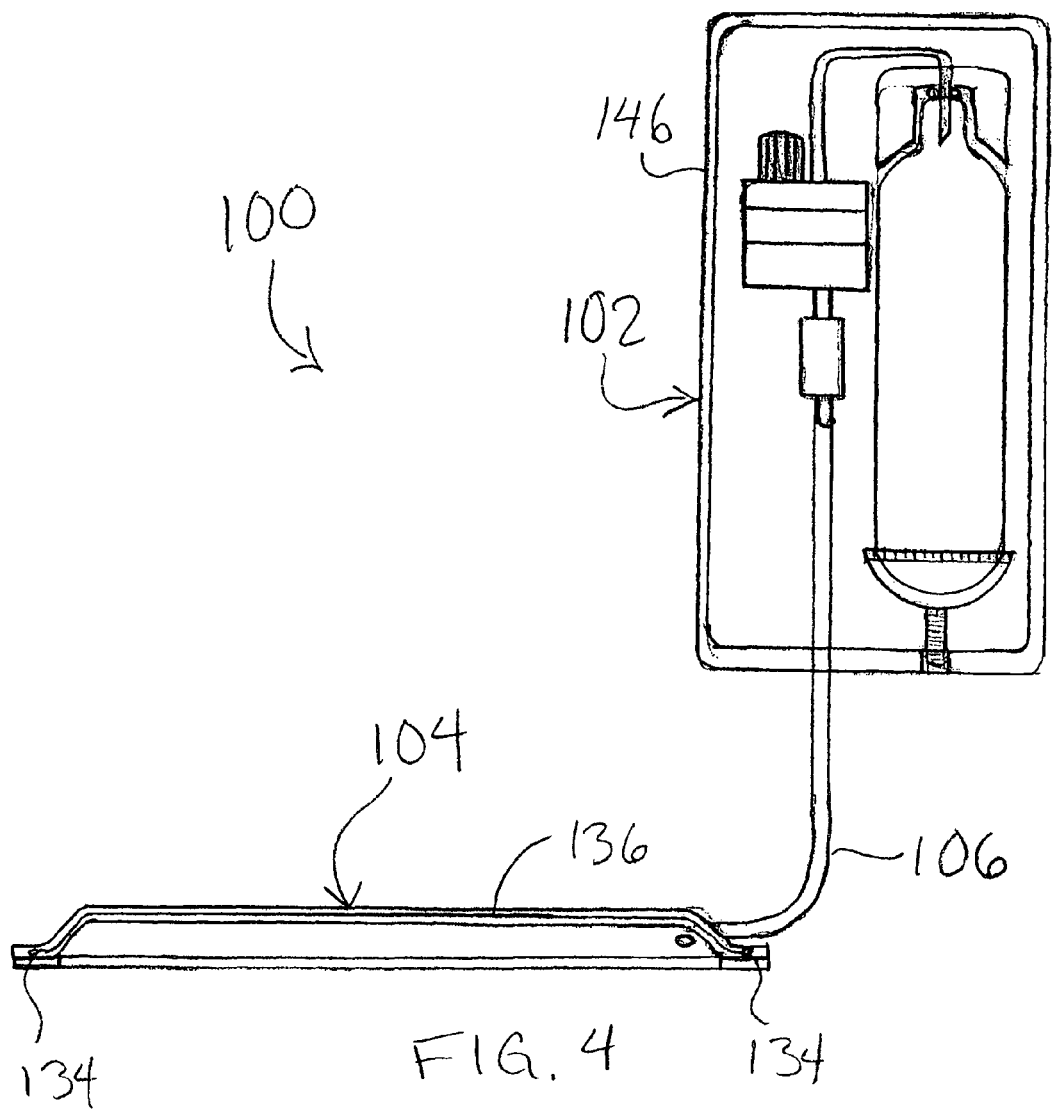
FIG. 4 shows a low-profile and form-fitting wound dressing capsule connected to the oxygen source by a flexible.

The topical oxygen therapy system 100 includes an oxygen source 102 and a wound dressing capsule 104. The oxygen source 102 may be attached directly to or integrated into the wound dressing capsule 104, as shown in FIGS. 1 and 2. FIG. 1 is a cutaway side view and FIG. 2 is a top view with a contoured protective housing 148 removed to show the oxygen source 102 inside. Alternatively, the oxygen source 102 and wound dressing capsule 104 may be separate modules connected by a flexible tube 106, as shown in FIGS. 3 and 4. The oxygen source 102, wound dressing capsule 104 and the flexible tube 106 may have luer fittings or quick connect/disconnect fittings 108 for easy assembly or revision of the system. The wound dressing capsule 104 can be circular, oval, square, rectangular, triangular or any convenient shape for covering the wound or wounds to be treated. The wound dressing capsule 104 can also be formed or formable into a tubular or cylindrical configuration to fit around a limb or another part of the patient's body.

In one preferred embodiment, the oxygen source 102 includes a miniature compressed oxygen 110 cylinder and a miniature pressure regulator 112 that delivers oxygen through an outlet tube 116 to the interior of the wound dressing capsule 104 (optionally connected via the flexible tube 106). In the current embodiment, the compressed oxygen cylinder 110 is approximately 2.5 inches long by 0.73 inches in diameter and contains oxygen compressed to approximately 3000 psi. Other sizes and pressures of the compressed oxygen cylinder 110 can also be used in the system. The miniature pressure regulator 112 is preferably adjustable for regulating the pressure to 0-20 psi, such that the oxygen source can supply a flow rate of 0-10 ml per hour of oxygen at atmospheric pressure or slightly above. Optionally, the oxygen source may include a calibrated orifice, an adjustable orifice, a porous flow restrictor or other flow control device 114 downstream from the pressure regulator 112 to control the flow rate of oxygen. Optionally, an on/off valve may also be included. At the current size, the compressed oxygen cylinder 110 has enough capacity for topical oxygen therapy over a period of approximately 5 days at a flow rate of 10 ml per hour, approximately 10 days at 5 ml per hour or approximately 17 days at 3 ml per hour. The necessary therapeutic flow rate will be determined primarily by the size of the wound dressing capsule needed to cover the wound or wounds being treated.

In an alternate embodiment, the oxygen source may utilize a fixed-pressure regulator. Coupled with a calibrated orifice, the fixed-pressure regulator will be able to deliver a reliable preset flow rate of oxygen.

The oxygen source with the compressed oxygen cylinder is small enough that it can be attached directly to or integrated into the wound dressing capsule, as in FIGS. 1 and 2. If the oxygen source is in a separate module, as in FIGS. 3 and 4, it can be placed in a protective housing 146 and it can be attached to the body adjacent to the wound dressing capsule or it can be clipped to the patient's belt or pinned to the patient's clothing. The entire treatment system weighs just a few ounces so the patient is free to walk around, work or exercise while the topical oxygen therapy is taking place on a continuous or intermittent basis. Keeping the patient ambulatory is especially important for maintaining circulation, which is important for the wound healing process, particularly in the lower limbs. It also reduces the overall cost of medical care because the patient can remain active and productive and does not need to interrupt his or her regular routine to receive therapy.

The compressed oxygen cylinder would typically be replaced approximately every 5 to 17 days, depending on the flow rate of oxygen used, but could be replaced more or less often if desired. Alternatively, two or more compressed oxygen cylinders may be provided in the oxygen source to provide longer therapy and/or higher flow rates. A hollow, tubular spike 118 connected to the pressure regulator pierces the tip of the compressed oxygen cylinder to connect to the interior of the cylinder while simultaneously creating a seal around the spike. Optionally, an O-ring or other sealing member 122 may be provided to help form a seal between the cylinder 110 and the tubular spike 118. Preferably, a mechanism 120 such as a screw, cam, lever or toggle is provided to increase the mechanical advantage for piercing the tip of the compressed oxygen cylinder. The mechanism can either move the cylinder toward the spike or the spike toward the cylinder. For safety, the mechanism also prevents the compressed oxygen cylinder from being detached from the spike while there is still pressure in the cylinder. One option is to configure the mechanism with an intermediate position where the pressure from the cylinder is allowed to safely vent before the cylinder is released.

Optionally, the oxygen source may be configured to mix the oxygen with ambient air to achieve oxygen levels in the range of 20 to 100 percent.

Optionally, the oxygen source may be configured to deliver more than one gas to the wound dressing capsule. The gasses could be mixed or they could be delivered sequentially or alternating. For example, nitrogen or carbon dioxide could be delivered initial and/or periodically to provide one or more periods of hypoxia or anoxia. Hypoxia has been shown to increase the release of tissue and vascular growth factors, which contribute to wound healing. Following the periods of hypoxia with periods of high oxygen concentration will accelerate the wound healing process. Another option would be to mix or alternate the delivery of oxygen with a gas that has other therapeutic effects. For example, nitric oxide can be administered to cause vasodilatation and increase perfusion of blood to the wound to accelerate healing.

Alternatively, the oxygen source may utilize a single cylinder of compressed mixed gas, for example a HELIOX or NITROX mixture.

The wound dressing capsule may be made in many different configurations. FIG. 3 shows a wound dressing capsule 104 in the shape of a rigid or semi-rigid dome 130 that covers and protects the wound during treatment. The base of the dome can be shaped to fit against the surface of a patient's limb, torso or other area to be treated.

In one alternative, the dome-shaped wound dressing capsule may be made of an impermeable elastic material that expands with the application of hyperbaric pressures, i.e. pressures above atmospheric pressure. The elastic energy stored in the dome can help to maintain the pressure within the wound dressing capsule. By closing an optional stopcock or one-way valve 132 on the inlet to the wound dressing capsule, the elastic material of the dome can maintain the internal pressure for an extended period of time, even when the oxygen source is disconnected.

The wound dressing capsule may include a pressure relief valve 124 to prevent overpressurization or the seal 126 may be configured to act as a pressure relief valve when excessive pressures are applied.

Optionally, the wound dressing capsule may be made with a port or a one-way valve 128 for establishing a connection with the interior of the wound dressing capsule without having to remove it. The port or valve can be used for introducing materials, such as moisture and medications. A syringe needle or a spray device can be inserted through the port or valve.

FIG. 4 shows a wound dressing capsule 104 that is lower profile and more form-fitting so that it can be worn unobtrusively under the patient's clothing. The wound dressing capsule 104 may be contoured to fit different body parts or it may be flexible so that it can be fitted to nearly any part of the patient's body. Optionally, a flexible wound dressing capsule may have a malleable member 134, such as an annealed copper or aluminum wire, embedded along the rim so that the wound dressing capsule can be manually shaped to fit against the surface of a patient's limb, torso or other area to be treated. Although this embodiment of the wound dressing capsule may be flexible, it is preferably not stretchable at the pressures used for therapy, otherwise the wound dressing capsule could balloon up conspicuously when pressurized. Optionally, support members 136, such as metal wires or more rigid plastic members or molded ribs, across the flexible wound dressing capsule will help to protect the wound and will help to keep the flexible wound dressing capsule from overinflating when internal gas pressure is applied.

The wound dressing capsule may be configured to allow application of hyperbaric, isobaric or hypobaric pressures. For applying different types of pressures, the wound dressing capsule should be impermeable to gas and should provide a good seal against the surface of the patient's body. For applying isobaric pressures, the wound dressing capsule may be permeable, impermeable or semipermeable and the seal against the surface of the patient's body is not as critical. For isobaric applications, the wound dressing capsule should be sufficient to maintain the desired concentration of oxygen at the wound site for a given flow rate of oxygen. Thus, there is a balance between flow rate of oxygen and permeability of the wound dressing capsule for maintaining effective wound healing therapy.

A sealing mechanism 126 may be provided for sealing the rim of the wound dressing capsule 104 against the patient's body surrounding the wound sufficiently to maintain the desired therapeutic concentration of oxygen at the wound site. The sealing mechanism 126 may be configure as a soft elastomeric rim seal, an elastomeric foam seal, an inflatable rim seal (inflated to a higher pressure than the treatment pressure), a fluid filled rim seal, etc. Preferably, the sealing mechanism is attached to the wound dressing capsule. Alternatively, a separate sealing mechanism may be used. For example, a sheet of sterile elastomeric foam can be cut to fit around the wound site, then the wound dressing capsule can be seated against the foam to provide a seal. For convenience, the sheet of foam may have contact adhesive on one or both sides. Alternatively or in addition to these mechanisms, the seal against the skin may be provided by a gel (solid or semi-solid) or a skin compatible, hyporeactive adhesive, such as a hydrocolloidal adhesive of the type used for ostomy devices, or adhesive tape. In some cases, high strength adhesives may be contraindicated because many patients with chronic wounds have fragile skin and injuries from adhesive removal would be slow to heal and could even become chronic wounds themselves.

Optionally, a protective layer, such as a hypo reactive dressing, can be applied to the skin prior to attaching the wound dressing capsule.

In an alternate embodiment, the wound dressing capsule may be a conventional occlusive dressing with the end of the flexible tube 106 placed under the dressing to deliver oxygen to the wound. The dressing may be covered with a permeable or semipermeable barrier layer to limit diffusion of the oxygen away from the wound area.

Figure 5:
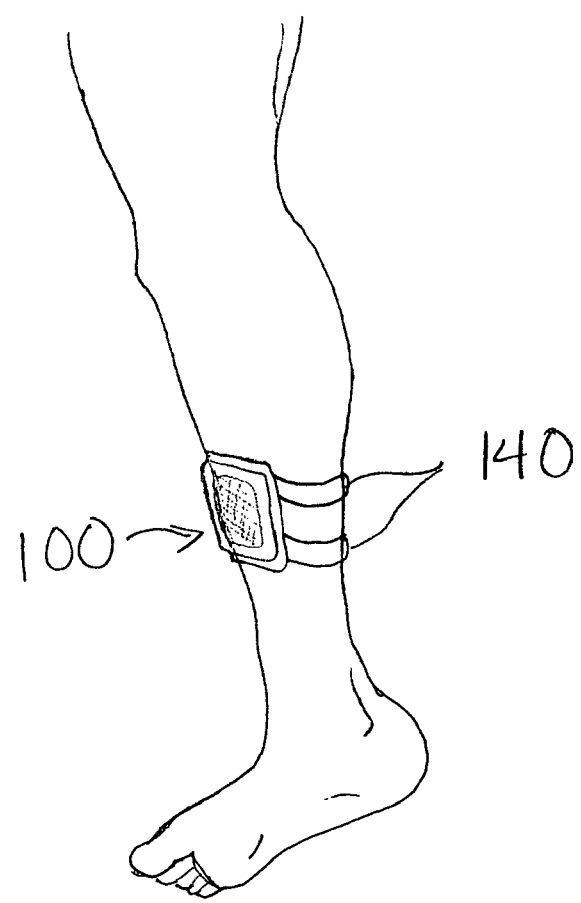
FIG. 5 shows a topical oxygen therapy system according to the present invention attached to a patient's lower extremity by a plurality of straps.

Alternatively or in addition to the attachment methods described above, one or more straps 140 may be provided to attach the topical oxygen therapy system 100 or the wound dressing capsule component of it to the patient, as shown in FIG. 5. Preferably, the straps would be made of a breathable, elastic material and could optionally include some foam padding or other cushioning material. The straps would wrap around the limb or torso of the patient and distribute the force of attachment so that pressure sores are not created. The straps may be attached to the wound dressing capsule or may simply wrap around it to hold it in place. The straps may attach using hook-and-loop fasteners, snaps, buckles, contact adhesive or other known fastening mechanisms. Alternatively, an elastic garment may be donned over the wound dressing capsule. As another alternative, adhesive tape may be used in place of the straps. The straps, in combination with a conformable rim seal and/or an adhesive, will help to hold the wound dressing capsule in place and to maintain hyperbaric pressures within the wound dressing capsule.

Hyperbaric pressures would more effectively drive oxygen into the tissues by diffusion. However, localized high pressure may interfere with blood circulation, as well as the migration of lymphocytes and fibroblasts into the area, therefore localized hyperbaric pressures should only be used intermittently. The oxygen source may be made programmable so that cyclic pressures are applied according to a treatment regimen. Alternating between hyperbaric, isobaric or hypobaric pressures can be accomplished using mechanically-actuated or electrically-actuated valves. The flow and/or pressure may be pulsed, which could improve the absorption of oxygen into the blood and tissues.

Alternatively, the wound dressing capsule may be configured to allow external manual or mechanical pressurization. The wound dressing capsule may be shaped like a bellows, telescopic structure or ambu that can be pressurized by pressing on it externally. Levers or other mechanisms may be used to increase mechanical advantage. Straps, latches, ratchets, springs or other mechanisms may be provided to maintain the pressure once it is applied. Alternatively, a motorized and/or automatic mechanism may be provided to mechanically increase or decrease the pressure according to a prescribed treatment regimen.

A port, reservoir or chamber 142 may be provided in the oxygen source and/or the wound dressing capsule to introduce humidity to keep the wound and the dressing moist because the compressed oxygen is likely to be very dry. Humidity can be provided in the form of water vapor or a mist introduced into the wound dressing capsule and or into the incoming flow of oxygen. An automated humidity control system may be provided with a moisture sensor, a water reservoir and an injector or evaporator.

Another port, reservoir or chamber 144 in the wound dressing capsule can also be used to introduce medication to the wound. The medication can be sprayed, injected or delivered to the surface of the wound. Medications can include topical anesthetics, antiseptics, antibiotics, healing promoters, such as nitric oxide, and/or tissue growth factors.

The topical oxygen therapy system can be used for intermittent or continuous delivery of oxygen and other gasses, depending on what treatment regimen is desired or found to be most effective. Typically, the wound dressing capsule will be applied over an absorbent wound dressing to absorb any exudate from the wound. Optionally, the absorbent wound dressing can be omitted for short-term or intermittent use of the topical oxygen therapy system to allow unrestricted contact between the oxygen and the wound and to allow observation of the wound during treatment. Optionally, the wound dressing capsule or a portion of it may be transparent to allow observation of the wound during treatment.

Optionally, the topical oxygen therapy system can include an electronic, mechanical or electromechanical control system to control and/or vary the pressure, flow rate, composition duration and timing of the topical oxygen therapy.

The topical oxygen therapy system can be configured to be reusable, with only the compressed oxygen cylinder needing to be replaced periodically. Alternatively, some or all of the topical oxygen therapy system, including the wound dressing capsule and/or the oxygen source, can be made disposable. As another alternative, the compressed oxygen cylinder can be made refillable by adding an inlet valve on the cylinder or otherwise connected to it so that the cylinder can be refilled from a larger compressed oxygen tank.

Topical oxygen therapy can be combined with other known modalities, for example subsonic, sonic or ultrasonic vibrations, photodynamic therapy or low level laser treatment. Optionally, the topical oxygen therapy system may include features to heat and/or cool the wound or the surrounding skin. For example, the tissue could be heated to increase local blood circulation or cooled to fight inflammation. Optionally, these additional features may be battery powered to allow maximum patient mobility.

While the present invention has been described herein with respect to the exemplary embodiments and the best mode for practicing the invention, it will be apparent to one of ordinary skill in the art that many modifications, improvements and subcombinations of the various features and embodiments, adaptations and variations can be made to the invention without departing from the spirit and scope thereof.

What is claimed is:

1. A portable topical oxygen therapy system, comprising:
   a miniature gas cylinder containing compressed oxygen;
   a miniature pressure regulator having an inlet and an outlet, the inlet of the pressure regulator connected to the gas cylinder; and a wound dressing capsule having an interior configured to cover or enclose an exterior portion of a patient's body, the interior of the wound dressing capsule being connected to the outlet of the pressure regulator;

wherein the portable topical oxygen therapy system is sized and configured to be wearable by the patient without interfering with normal ambulation and wherein the miniature gas cylinder and the pressure regulator are integrated into the wound dressing capsule as a single wearable unit.

2. The portable topical oxygen therapy system of claim 1, further comprising:
a flow restrictor connected between the outlet of the pressure regulator and the interior of the wound dressing capsule.

3. The portable topical oxygen therapy system of claim 1, wherein the pressure regulator provides an adjustable outlet pressure in a range of 0-20 PSI.

4. The portable topical oxygen therapy system of claim 1, wherein the pressure regulator provides a fixed outlet pressure in a range of 0-20 PSI.

5. The portable topical oxygen therapy system of claim 1, wherein the pressure regulator provides a flow rate of oxygen of 0-10 ml/hour to the interior of the wound dressing capsule.

6. The portable topical oxygen therapy system of claim 1, wherein the wound dressing capsule is dome-shaped.

7. The portable topical oxygen therapy system of claim 1, further comprising:
a pressure relief valve configured to release gas when pressure within the interior of the wound dressing capsule exceeds a predetermined level.

8. The portable topical oxygen therapy system of claim 1, further comprising:
a sealing mechanism to seal a rim of the wound dressing capsule to the patient's skin.

9. The portable topical oxygen therapy system of claim 8, wherein the sealing mechanism is configured to act as a pressure relief valve by releasing gas when pressure within the interior of the wound dressing capsule exceeds a predetermined level.

10. The portable topical oxygen therapy system of claim 8, wherein the sealing mechanism comprises a soft elastomeric rim seal.

11. The portable topical oxygen therapy system of claim 8, wherein the sealing mechanism comprises an elastomeric foam seal.

12. The portable topical oxygen therapy system of claim 8, wherein the sealing mechanism comprises an inflatable rim seal.

13. The portable topical oxygen therapy system of claim 8, wherein the sealing mechanism comprises a fluid filled rim seal.

14. The portable topical oxygen therapy system of claim 1, wherein the wound dressing capsule is, impermeable.

15. The portable topical oxygen therapy system of claim 1, wherein the wound dressing capsule is permeable.

16. The portable topical oxygen therapy system of claim 1, wherein the wound dressing capsule is semipermeable.

17. The portable topical oxygen therapy system of claim 1, further comprising:
a strap for attaching the wound dressing capsule to the patient.

18. The portable topical oxygen therapy system of claim 1, further comprising:
a port configured for introducing materials into the interior of the wound dressing capsule without removing the wound dressing capsule from the patient.

19. The portable topical oxygen therapy system of claim 1, further comprising:
a one-way valve configured for introducing materials into the interior of the wound dressing capsule without removing the wound dressing capsule from the patient.

20. The portable topical oxygen therapy system of claim 1, wherein the wound dressing capsule is flexible, whereby the wound dressing capsule can be shaped to fit against a surface of the patient's body to be treated.

21. The portable topical oxygen therapy system of claim 1, further comprising:
a malleable member embedded along a rim of the wound dressing capsule, whereby the wound dressing capsule can be shaped to fit against a surface of the patient's body to be treated.

22. The portable topical oxygen therapy system of claim 1, further comprising:
means for cycling pressures in the interior of the wound dressing capsule according to a predetermined treatment regimen.

23. The portable topical oxygen therapy system of claim 1, further comprising:
means for cycling pressures in the interior of the wound dressing capsule between hyperbaric, isobaric and/or hypobaric pressures according to a predetermined treatment regimen.

24. The portable topical oxygen therapy system of claim 1, further comprising:
means for pulsing pressures in the interior of the wound dressing capsule.

25. The portable topical oxygen therapy system of claim 1, further comprising:
means for manually pressurizing the interior of the wound dressing capsule.

* * * * *